United States Patent [19]

Giddens

[11] Patent Number: 5,050,440

[45] Date of Patent: Sep. 24, 1991

[54] PROCESS AND APPARATUS FOR SAMPLING GAS-ENTRAINED PARTICULATE MATERIALS

[75] Inventor: Anthony B. Giddens, Birchwood, Tenn.

[73] Assignee: E. I. du Pont de Nemours and Company, Wilmington, Del.

[21] Appl. No.: 564,588

[22] Filed: Jun. 29, 1990

[51] Int. Cl.⁵ .............................................. G01N 1/14
[52] U.S. Cl. .................................................. 73/863.83
[58] Field of Search ................ 73/864, 864.33, 864.51, 73/863.81, 863.41, 863.71, 863.82, 863.83

[56] References Cited

U.S. PATENT DOCUMENTS 4,286,466 9/1981 Stewart .......................... 73/863.83

OTHER PUBLICATIONS

Manual describing a Model PT sampler sold by Intersystems Industrial Products, Inc. (Oct. 1983).

Primary Examiner—Jerry W. Myracle

[57] ABSTRACT

A process and apparatus for sampling a stream of gas-entrained particulate matter are provided. A sampling tube is employed which has an inlet exposed to the gas-entrained stream and extending to an outlet in a sample receiver. Pressurized gas is introduced into the sampling tube between the inlet and the outlet and is directed toward the sample receiver so that gas acts to decrease the gas pressure present at the inlet of the sampling tube to substantially continuously draw the particulate matter into the tube and deposit it in the sample receiver. So that a sample of a desired size can be collected over a given time period, the rate at which the particulate matter is drawn into the sampling tube is adjusted. The sample receiver provides for venting gas while retaining the sampled particulate matter.

14 Claims, 1 Drawing Sheet

PROCESS AND APPARATUS FOR SAMPLING GAS-ENTRAINED PARTICULATE MATERIALS

BACKGROUND OF THE INVENTION

The present invention relates to a method and apparatus for sampling gas-entrained particulate materials and more particularly relates to a method and apparatus for sampling gas entrained particulate materials in which the stream of gas-entrained particulate matter is continuously sampled.

Nylon polymer which is prepared in an autoclave polymerization vessel is ordinarily extruded from this vessel in a molten state, quenched with water for solidification and chopped into pieces known as flake. The extrusion, quenching and chopping steps are often referred to as flake "casting". The flake form of the polymer is readily processed further into other articles such as, e.g., fiber.

Since the autoclave process is a batch process, it is known to be subject to variability which may affect the properties of the flake produced by the process. For this reason, there is a need to sample each batch of flake during a casting process to perform off-line analyses. These analyses may include measurement of polymer viscosity and the determination of amine and/or carboxyl end concentration. The need to collect a flake sample for analysis which accurately represents the material produced in each batch is a well-recognized part of any analytical protocol. That is, a sample of flake must be obtained during the course of extrusion which is representative of the first kilogram of material cast, as well as, the last kilogram of polymer to exit the vessel. It is well-known that a profile of properties, like relative viscosity, may be present in the polymer extruded from the autoclave. By sampling the flake extruded over the approximately 20 minute span of casting, a representative sample of the entire is obtained.

Sampling systems which can be used for nylon flake are commercially available. For example, Intersystems Industrial Products, Inc., 17330 Preston Road, Dallas, Tex. 75252 manufactures the Model PT sampler which grabs flake samples at timed intervals from an air-entrained stream of nylon flake using a solenoid-controlled air cylinder to push a sampling tube into the product stream. A cavity in the sampling tube gathers the sample, the tube is retracted and the sample is eventually conveyed by gravity to a sample container. Using this equipment, samples can be collected at about 30 second intervals during which the sample tube is exposed to the quenched flake stream for about 1 second. Over the course of a typical 20 minute casting run about 40 such samples are obtained which are then pooled to provide a sample of about 300 grams. However, the necessary intervals between each sample means that the pooled sample is not truly representative of the entire flake casting run. Furthermore, such mechanical sampling systems are complex, have a number of moving parts, and require frequent maintenance. The compressed air system containing a high level of stored energy can also be dangerous when repair or adjustment of such samplers is being performed.

SUMMARY OF THE INVENTION

In accordance with the invention, a process and apparatus for sampling a stream of gas-entrained particulate matter such as air-entrained nylon flake are provided. A sampling tube is employed which has an inlet exposed to the gas-entrained particulate matter stream and which extends to an outlet in a sample receiver. Pressurized gas is introduced into the sampling tube between the inlet and the outlet and is directed toward the sample receiver so that the gas acts to decrease the gas pressure present at the inlet of the sampling tube to substantially continuously draw the particulate matter into the tube and deposit it in the sample receiver. So that a suitably-sized sample can be collected over a desired time period, provision is made for adjusting the rate at which the particulate matter is drawn into the sampling tube. The sample receiver provides for venting gas while retaining the particulate matter.

In accordance with a preferred process and apparatus, the particulate matter in the sample receiver is agitated. Most preferably, agitating is performed by directing pressurized gas into the receiver to turbulently mix the particulate matter. The agitation pressurized gas is controlled so that turbulent mixing is done periodically.

In accordance with another preferred form of the invention for sampling a stream gas-entrained particulate matter in which the the density of the particulate matter varies with location in the stream, the rate at which the particulate matter is drawn into the the sampling tube is adjusted by adjusting the position of the inlet of the sampling tube in the stream.

The invention provides a process and apparatus for the sampling of gas-entrained particulate matter such as air-entrained nylon flake which requires no moving parts. The desired sample size is easily provided while substantially continuously sampling the material in the stream. The invention is inexpensive to implement and inherently safe to operate.

DETAILED DESCRIPTION

Figure 1:
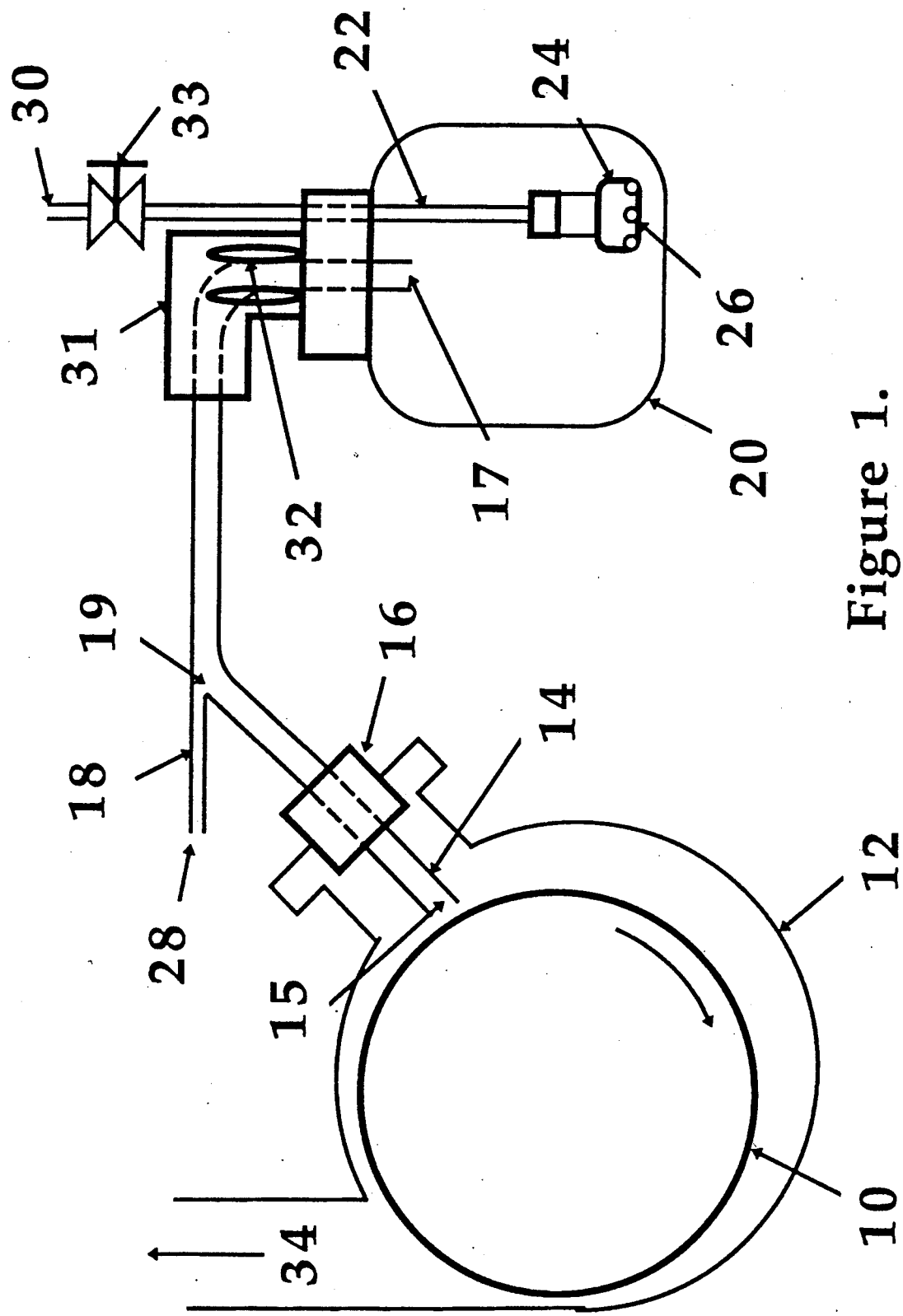
FIG. 1 is a diagrammatical, cross-sectional view in elevation of a preferred form of sampling apparatus in accordance with the present invention for sampling air-entrained nylon flake in a dewatering fan cylinder.

Referring now to FIG. 1, a dewatering fan cylinder 12 for nylon flake is shown diagrammatically in cross-section. An elongated fan 10 mounted within the cylinder in a non-coaxial position for rotation in the direction of the arrow serves to convey nylon flake entrained in flow of air moving in a direction perpendicular to cylinder 12. Wet flake enters the cylinder at one end adjacent the extruder, strand cutter and quench area (not illustrated) and is dewatered as it moves in an air stream and ultimately exits the dewatering fan cylinder at its other end at outlet 34 in the direction of the arrow.

In accordance with a preferred form of the invention, flake is drawn substantially continuously from the stream of air-entrained flake in the dewatering cylinder 12 through sampling tube 14 having an inlet 15 exposed to the stream within the cylinder 12. "Drawn substantially continuously" as used in this application is intended to mean that the inlet 14 is open and operable to draw flake from the stream but there may be small, random time intervals between when flakes actually enter the inlet 14. As will be explained in more detail hereinafter, tube 14 is variably positioned in the cylinder 12 to adjust the position of the inlet 15 in relation to the periphery of fan 10. This is suitably accomplished by slidably mounting the tube 14 in bulkhead fitting 16. The sampling tube 14 extends from the cylinder 12 to a sample receiver 20 which is dimensioned to hold the desired sample size. An outlet 17 of the sampling tube 14 is provided within the sample receiver 20 for discharging the flake.

An injection port 19 is provided in the sampling tube between the inlet 15 and outlet 17 for introducing a pressurized gas such as air from a source (not illustrated) into the sampling tube 14. The air is directed into the tube 14 toward the sample receiver so that the increased air velocity acts to decrease the pressure present at the inlet 14 of the sampling tube to substantially continuously draw the flake into the tube 14 and deposit it into the sample receiver 20. The injection port 19 illustrated is formed by tube 18 which joins the tube 14 at an obtuse angle bend and is supplied with pressurized air at 28 as indicated by the arrow.

In order to collect a sample representative of the entire flake casting run with a given sample receiver size, the rate at which the sample is drawn into the sampling tube is adjusted. This can be done in a number of ways such as by selecting the size of the sampling tube inlet, changing the air pressure supplied at point 28, etc. When the stream of entrained materials has a density which varies with location in the stream, it is preferable for the location of the inlet 15 of the sampling tube 14 to be moved to change the sampling rate. In the apparatus illustrated, there is a radial density gradient of polymer flake in cylinder 12 with the density being smallest adjacent the fan 10 and greatest adjacent the walls of the cylinder 12. The inlet 15 of tube 14 is positioned by sliding the tube 14 in the bulkhead fitting 16 to sample a more or less dense region of flake to adjust the sampling rate. When the same equipment for flake production and sampling is used repeatedly a similar manner it may be possible to adjust the position of the sampling tube initially and use the same adjustment for subsequent runs.

After a sample of flake is collected during the course of a flake casting operation, the pressurized air at point 28 is stopped. Since the lower pressure at the inlet 15 will no longer be present, sampling of the flake stops. The sample is then agitated to eliminate any stratification in the sample receiver 20. This is preferably accomplished by introducing a pressurized gas such as air into the sample receiver 20 to cause turbulent mixing. As illustrated, pressurized air is introduced at point 30 into a tube 22 and is controlled by valve 33 so that turbulent mixing is done periodically. Tube 22 is connected to pipe cap 24 which has several orifices 26 to allow the compressed air to exit the tube and turbulently mix the collected polymer flake. Typically, a radial arrangement of, for example, six such orifices is suitable. Vents 32 provided in the sample receiver 20 such as in pipe elbow 31, which supports the sample receiver 20, serve to vent the pressurized air when introduced at either point 28 or 30. The vents 32 are sized so that sufficient air flow occurs but polymer flake cannot pass through and is retained in the sample receiver 20.

EXAMPLE

During a 1250 kg nylon flake casting run, the apparatus illustrated in FIG. 1 is used to collect a sample of flake weighing about 300 grams and having a mean size of 5 mm × 5 mm × 2 mm per flake. Tube 14 is made of stainless steel with an inside diameter of ¾ inch and is believed to allow passage of about one polymer flake at a time through tube 14. For a batch size of 1250 kg, 90 gauge psi of air is supplied to tube 18 from point 28 into tube 14 for 20 minutes. With the fan rotating at 2650 rpm, the inlet 15 of tube 14 is positioned about ¾ inch away from the periphery of fan 10. Typically, it has been found that this positioning of the inlet in the cylinder 12 in relation to the fan 10, yields the desired 300 gram sample continuously collected over the full 20 minute span of the flake casting operation.

At the end of a typical 20 minute sampling time period, the compressed air introduction at 18 is stopped to stop the sampling and 90 psi air is introduced at point 30 into tube 22. The resultant turbulent mixing thoroughly mixes the sample and ensures that any stratification of the sampled flake is removed. The sample receiver 20 is then disconnected from elbow 31 and the sampled flake is sent for off-line quality control testing.

While a preferred embodiment has been shown and described in the foregoing detailed description, it will be understood that the invention is capable of numerous modifications, rearrangements and substitution of parts without departing from the spirit of the invention as set forth in the appended claims.

I claim:

1. Apparatus for sampling a stream of gas-entrained particulate matter comprising:
   a sample receiver;
   a sampling tube having an inlet exposed to the stream of gas-entrained particulate matter and extending to an outlet in said sample receiver;
   a source of pressurized gas;
   gas injection port between said inlet and outlet which introduces said pressurized gas into said sample tube and directs said gas toward said sample receiver, the introduction of said gas acting to decrease the gas pressure present at the inlet of said sampling tube to induce the particulate matter to be substantially continuously drawn into said tube and deposited into said receiver;
   means for adjusting the rate at which the particulate matter is drawn into said sampling tube; and
   vent means for venting gas introduced into said receiver while retaining the particulate matter in said receiver.

2. The apparatus of claim 1 further comprising means for agitating the particulate matter in said receiver.

3. The apparatus of claim 2 wherein said means for agitating comprises means for directing pressurized gas into said receiver to turbulently mix the particulate matter and valve means for controlling said pressurized gas so that turbulent mixing is done periodically.

4. Apparatus for sampling a stream of gas-entrained particulate matter in which the density of the particulate matter varies with location in the stream comprising:
   a sample receiver;
   a sampling tube having an inlet exposed to the stream of gas-entrained particulate matter and extending to an outlet in said sample receiver;
   a source of pressurized gas;
   gas injection port between said inlet and outlet which introduces said pressurized gas into said sample tube and directs said gas toward said sample receiver, the introduction of said gas acting to decrease the gas pressure present at the inlet of said sampling tube to induce the particulate matter to be substantially continuously drawn into said tube and deposited into said receiver;
   means for adjusting the position of said inlet of said sampling tube in said stream to locations with differing densities of particulate matter to adjust the rate at which particulate matter is drawn into said sampling tube; and vent means for venting gas introduced into said receiver while retaining the particulate matter in said receiver.

5. The apparatus of claim 4 further comprising means for agitating particulate matter in said receiver.

6. The apparatus of claim 5 wherein said means for agitating comprises means for directing pressurized gas into said receiver to turbulently mix said particulate matter and valve means for controlling said pressurized gas so that turbulent mixing is done periodically.

7. A process for sampling a stream of gas-entrained particulate matter comprising:

providing a sample receiver;

providing a sampling tube having an inlet exposed to the gas-entrained stream and extending to an outlet in said sample receiver;

introducing pressurized gas into said sampling tube between said inlet and said outlet and directing said gas toward said sample receiver so that gas acts to decrease the gas pressure present at the inlet of said sampling tube to substantially continuously draw the particulate matter into said tube and deposit it in said receiver;

adjusting the rate at which the particulate matter is drawn into said sampling tube so that a desired sample size is collected over a given time period; and venting gas introduced into said receiver while retaining the particulate matter in said receiver.

8. The process of claim 7 further comprising agitating the particulate matter in said receiver.

9. The process of claim 8 wherein said agitating is performed by directing pressurized gas into said receiver to turbulently mix said particulate matter and controlling said pressurized gas so that turbulent mixing is done periodically.

10. The process of claim 7 wherein the particulate matter is nylon flake.

11. A process for sampling a stream of gas-entrained particulate matter in which the density of the particulate matter varies with location in the stream comprising:

providing a sample receiver;

providing a sampling tube having an inlet exposed to the gas-entrained stream and extending to an outlet in said sample receiver;

introducing pressurized gas into said sampling tube between said inlet and said outlet and directing said gas toward said sample receiver so that gas acts to decrease the gas pressure present at the inlet of said sampling tube to substantially continuously draw the particulate matter into said tube and deposit it in said receiver;

adjusting the position of said inlet of said sampling tube in the stream to a location with a density of particulate matter such that the rate at which the particulate matter is drawn into said sampling tube is such that a desired sample size is collected over a given time period; and venting gas introduced into said receiver while retaining the particulate matter in said receiver.

12. The process of claim 11 further comprising agitating the particulate matter in said receiver.

13. The process of claim 12 wherein said agitating is performed by directing pressurized gas into said receiver to turbulently mix said particulate matter and controlling said said pressurized gas so that turbulent mixing is done periodically.

14. The process of claim 11 wherein the particulate matter is nylon flake.

* * * * *